(12) United States Patent
Johnson

(10) Patent No.: US 6,907,617 B2
(45) Date of Patent: Jun. 21, 2005

(54) GOGGLE SHIELD

(75) Inventor: Matthew A. Johnson, St. Louis, MO (US)

(73) Assignee: Eagle Industries Unlimited, Inc., Fenton, MO (US)

( * ) Notice: Subject to any disclaimer, the term of this patent is extended or adjusted under 35 U.S.C. 154(b) by 154 days.

(21) Appl. No.: 10/248,595

(22) Filed: Jan. 30, 2003

(65) Prior Publication Data

US 2003/0145368 A1 Aug. 7, 2003

Related U.S. Application Data

(60) Provisional application No. 60/353,143, filed on Feb. 1, 2002.

(51) Int. Cl.[7] .................................................. A61F 9/00
(52) U.S. Cl. ................................................ 2/13; 206/5
(58) Field of Search .......................... 2/13, 426; 206/5; 224/255

(56) References Cited

U.S. PATENT DOCUMENTS

| | | | | |
|---|---|---|---|---|
| 4,606,453 A | * | 8/1986 | Burns ............................. | 206/5 |
| 4,953,695 A | * | 9/1990 | Tallman ......................... | 206/5 |
| 5,344,002 A | * | 9/1994 | Baczkowski ................... | 206/5 |
| 5,593,024 A | * | 1/1997 | Seiler ............................ | 206/5 |
| 5,735,393 A | * | 4/1998 | Shiue et al. ................... | 206/5 |

* cited by examiner

*Primary Examiner*—Katherine M Moran
(74) *Attorney, Agent, or Firm*—Blackwell Sanders Peper Martin LLP

(57) ABSTRACT

A goggle shield is provided. The shield includes a lined cover, and multiple attachment devices to attach the cover to a goggle. The cover may be easily moved from a shielding position over the goggle lens to permit viewing through the goggle lens. Resilient means is provided to permit selective adjustment of the size and shape of the cover allowing the cover to be fit to various sizes and shapes of goggles. The attachment devices are operable to allow a user various modes of operation of the shield.

26 Claims, 3 Drawing Sheets

GOGGLE SHIELD

CROSS REFERENCE TO RELATED APPLICATIONS

This application is a non-provisional application based on Provisional Application Ser. No. 60/353,143, filed Feb. 1, 2002 for A GOGGLE SHIELD.

BACKGROUND OF THE INVENTION

Goggles are commonly used as eye protection for military personnel, athletes, workers and the like. In order to improve to provide good vision for the user, it is desirable to prevent scratching of the goggle lens. Improvements in polymers and polymer coatings in recent years has improved the scratch resistance of polymeric lenses, however, they still can scratch obscuring the user's vision. The use of a glass lens in goggles, even though scratch resistant, is not necessarily desirable since glass can be broken and shatter possibly causing eye injury to the goggle user. Goggles are carried by users in at least three ways. They may be worn by the user in an eye covering position. They may also be moved to an elevated position on the forehead or a lowered position around the neck when not needed for eye protection. Also, goggles may be carried in a pocket, backpack, fanny pack or the like by a user when not in use. Regardless of carrying mode, the lens needs to be protected from unnecessary damage. Frequently, goggles are carried by users more in a non-use manner than in a use manner thus exposing the lens to possible damage for extended periods of time and increasing the likelihood of damage to the lens. When carried, goggles may have the lens covered, as for example, by a bag or case in which they may be placed to shield the lens.

When goggles are used in high stress situations, little time may be available for removing the goggles from the bag or case to allow the wearer to use the goggles. Because each user of goggles may have a preference for how to best use a lens protective device, an advantageous protective device would allow for multiple modes of use. Further, there are many types and styles of goggles available for use and it would be preferable to have a universally adaptable shield that can be attached to and used on existing goggles, i.e., providing the ability to retrofit without modification to the goggles or shields and on new goggles.

Further, it is not uncommon for a goggle lens to become dirty during non-use or use and it would be desirable to provide a means for cleaning the lens in a convenient manner.

Particularly for military applications, a goggle shield would be constructed to provide for its securement to the goggle in a removable manner for both replacement and initial installation.

SUMMARY OF THE INVENTION

The present invention involves the provision of a shield for attachment to a goggle to selectively protect the exterior surface of the lens thereof. The shield includes a cover and an elastic means for resiliently retaining the cover in overlying relation to the goggle lens. The elastic member gathers the material of the cover shortening an extended length of the cover thereby forming the cover into a cup having resiliently stretchable top and bottom margins. The margins engage upper and lower portions of the goggle body forming a seal therebetween to reduce the ingress of dirt and debris between the cover and goggle lens. Straps may be provided at the ends of the cover and clips may be provided for releasably attaching the shield to the goggle strap on opposite sides of the lens. Also, a third attachment device may be provided, for example, a hook and loop fastener device one portion of which is secured to the goggle preferably, the strap, and one portion to part of the shield to allow the cover to be released on one end. The free end can be attached to, for example, the strap, securing the cover in an out of the way position to the side of the goggle.

A lining may be provided to be positioned between the cover and the goggle lens. Such lining is of a non-abrasive material to help reduce damage to the goggle lens. The lining may be of a microfiber material adapted for cleaning the lens or a fleece material. The lining may be of high nap, medium nap or low nap fabric. A low nap fabric is preferred for cleaning.

These and other aspects and advantages of the present invention will become apparent upon reading the detailed description in connection with the drawings and the appended claims.

BRIEF DESCRIPTION OF THE DRAWINGS

Corresponding reference numerals designate like or similar parts throughout the various figures of the drawings.

DETAILED DESCRIPTION

Figures 1, 5:
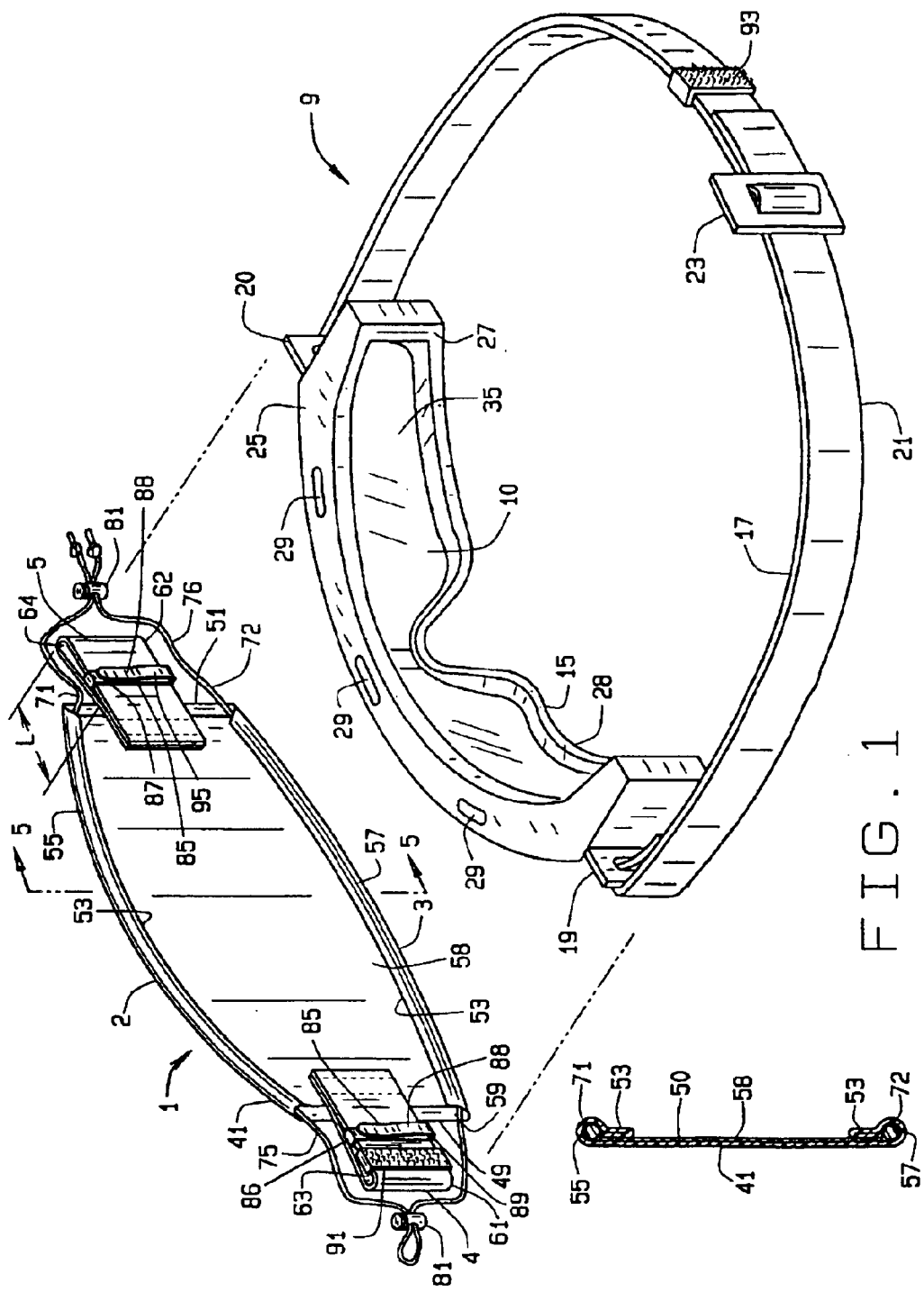
FIG. 1 is a perspective view of a goggle shield and goggle viewed from the inside surface.
FIG. 5 is a cross sectional view taken along the line 5—5 of FIG. 1.

The reference numeral 1 designates generally a goggle shield having top and bottom margins 2 and 3 respectively, and opposite ends 4 and 5. The goggle shield 1 is adapted for mounting on a goggle 9 in overlying relationship to a goggle lens 10. The goggle 9 may be mounted on a helmet or the like or may be worn bare headed or over a hat by a user.

The goggle 9 includes a body 15 having the lens 10 mounted in the front portion of the body. A strap 17 is provided with opposite ends of the strap extending from opposite ends 19, 20 of goggle body 15. Typically the strap 17 includes an elastic section 21 and a buckle 23 and may be separated into two parts at the buckle. The length of the strap 17 may be adjusted in the buckle 23 as is well known in the art. Although a simple goggle arrangement is illustrated, any suitable form of goggle may be utilized with the present invention. Goggle body 15 has an upper surface 25 extending between the lens 10 to a face engaging portion 27. The lower portion of the goggle includes a bottom surface 28 extending from the lens 10 to the face engaging portion 27. The spacing between the lens 10 and the face engaging portion 27 can be on the order of ½ to ¾ inch. Generally, the body 15 includes a lightweight foam material, soft polymer or soft rubber to help the goggle conform to the user's face shape and contour. Vents 29 may also be provided in the body 15 if desired to provide face ventilation for the user. However, the vents 29 can also permit the ingress of dirt and debris into the interior 35 of the goggle. This may cause the user a problem when the goggle is moved to an eye covering and shielding position.

The goggle shield 1 includes a cover 41. The cover 41 is preferably somewhat oval shaped since goggles tend to have somewhat of an oval shape themselves. The cover 41 is preferably made of a tightly woven fabric such as a 420 denier nylon. Such a material provides durability plus a tight weave which will prevent large dirt particles and debris from passing therethrough to the lens 10 when in covering relation to the lens 10. A woven fabric also provides for breathability. However, it is to be understood that other suitable types of fabric or material may be used. The cover includes the top and bottom marginal portions 2, 3 extending between opposite ends 49, 51. Because the cover 41 is fabric, it may be folded over and sewn to form seams 53. An upper channel and lower channel 55, 57, respectively, are formed at the marginal portions 2, 3 for a purpose later described.

In a preferred embodiment, a liner 58 overlies an interior surface 59 of the cover and is held in place by being sewn at the seams 53. The liner 58 is preferably a soft flexible fabric that is non-abrasive. Particularly preferred fabrics include polyester fleece which is particularly adapted for use in environments where dirt and debris are small and will not be retained in the nap of the fabric. Another preferred fabric is what is referred to as a microfiber. Such a fabric is typically a low nap fabric. Because of the fineness of the fibers, the fabric is very effective at cleaning dirt including oils from eyeglass lenses and the like. Such materials are well known in the art. Microfiber materials can also be provided in a high or medium nap version which may also be used for the liner 58 and are also effective for cleaning. The particular liner material utilized will be determined by the environment in which the shield is anticipated to be used. For example, in an arctic or snowy environment, a high nap microfiber or fleece may be used since very little abrasive material would be in the environment to damage the lens 10. A low nap fiber may be used in an environment, say for example, in a desert environment where grit might become entrained in the liner if it were high or medium nap. Preferably, the size and shape of the liner 58 is approximately those of the lens to avoid wasting material but the size is preferably slightly larger to ensure it contacts the lens to help reduce possible damage to the lens.

The shield 1 includes a pair of end straps 61, 62 attached to opposite ends of the cover 41. The straps 61, 62 are preferably of a fabric and elastic material combination. Straps 61, 62 are each preferably in the form of a loop having opposite ends of each strap sewn or otherwise attached to the cover 41. Openings 63, 64 extend through the loop of the straps 61, 62 respectively. The straps 61, 62 are generally in the plane of the cover 41 when flat. The length L (FIG. 1) of the openings 63, 64 in the straps are preferably on the order of ¾ inch to 2 inches. The loops formed by the straps are for a purpose hereinafter described.

Resiliently deformable or elastic upper and lower members 71, 72, respectively, each extend through a respective channel 55, 57 having portions thereof positioned outside of the respective channel preferably forming loops 75, 76 at opposite ends 49, 51 of the cover 41. A single elastic member may be used or two separate elastic members may be used. A preferred elastic member is a shock cord having a diameter in the range of between about ⅛ and 3/16 inch. The cover 41 may be gathered at its marginal portions 2, 3 by having the shock cord segments within the channels 55, 57 shorter than the extended length of the respective channel. By gathering the material at the marginal portions 2, 3, the cover 41 and the attached lining will assume a cup shape. Thus, the lengths of the channels 55, 57 may be elastically or resiliently shortened. By stretching the elastic member, the shortened length of the cover 41 may be selectively extended in a resilient manner. A lock device 81 can be attached to one or more of the members 71, 72 at one or both of the loops 75, 76. Preferably there is a lock 81 at each end of the cover 41. A suitable lock 81 may be what is referred to in the industry as a barrel lock or toggle lock. Such a lock 81 has a depressible button that selectively releases an elastic member from retention in the lock allowing the lock to be moved along the elastic member to provide adjustable tension. Release of the button fixes the lock in position on the elastic member. By gathering the cover 40 at the margins 2, 3, the cover and the attached lining will assume a cup shape.

The size and shape of the cover are such that when the shield 1 is attached to the goggle in overlying relationship to the lens 10, the cover 41 will extend over the surfaces 25, 28. The margins 2, 3 provide a seal between the cover 41 and the goggle body 15 to reduce the ingress of dirt and debris to a position between the liner 58 and the lens 10 and to seal the vents 29. Use of elastically deformable members with the cover allow the cover 41 to be attached to the goggle 9 for easy movement by the wearer of the cover to permit viewing through the lens 10 of the goggle.

Figure 4:
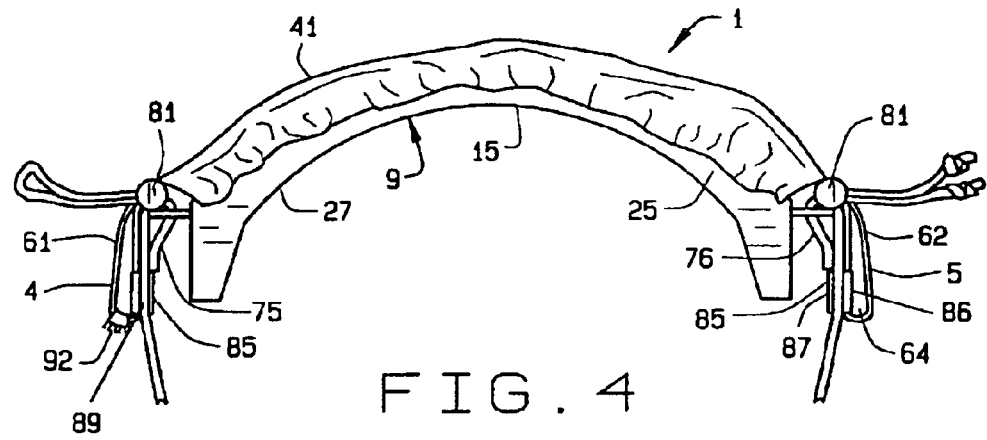
FIG. 4 is a view similar to FIG. 2 showing a third mode of shield attachment to the goggle.

One or more suitable attachment members such as attachment devices 85 are provided to attach the cover 41 to the goggle 9. The preferred attachment device 85 includes a clip having a clip body 86 with a respective strap slot 87 therethrough. It is preferred that the attachment device 85 be moveable along the length of the respective strap to provide an adjustable and/or snug fit of the shield 1 to the goggle 9. Attachment device 85 further includes a resilient finger 88 attached to the body defining a slot therebetween having an open end. The finger 88 and body 86 have an open ended slot 89 (FIG. 1) therebetween and preferably engage one another in an area therebetween to provide frictional engagement between the attachment device 85 and the goggle strap 17 when installed thereon by inserting the goggle strap 17 into a respective slot 89. By a simple straight pull, the goggle strap may be released from the slot 89 allowing removal of the cover 41 from the goggle 9 when attached as shown in FIG. 4. The use of the devices 85 to solely attach the shield 1 to the goggle 9 is shown in FIG. 4.

Figure 2:
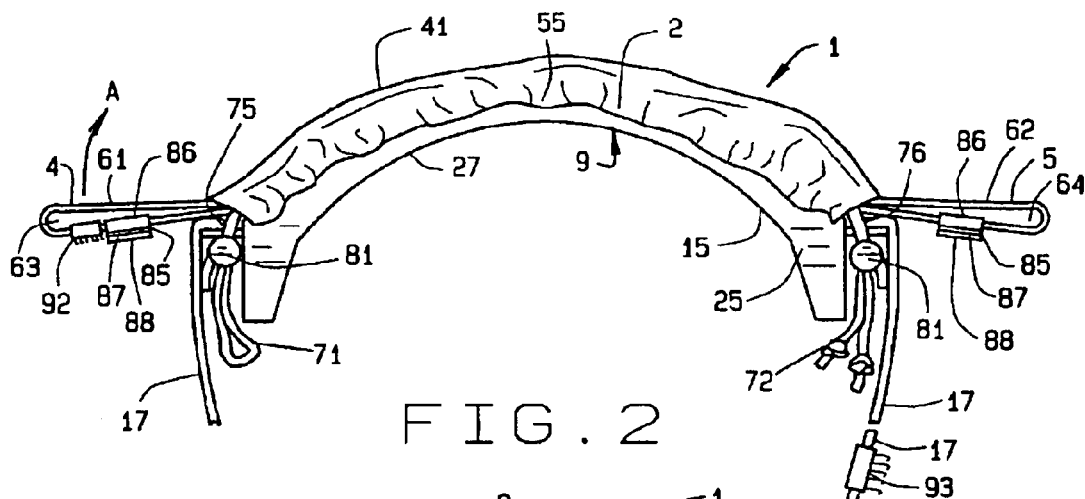
FIG. 2 is a plan view of a goggle shield attached to a goggle with the shield being shown in a lens protective position, the figure illustrating one mode of shield attachment to the goggle.
Figure 3:
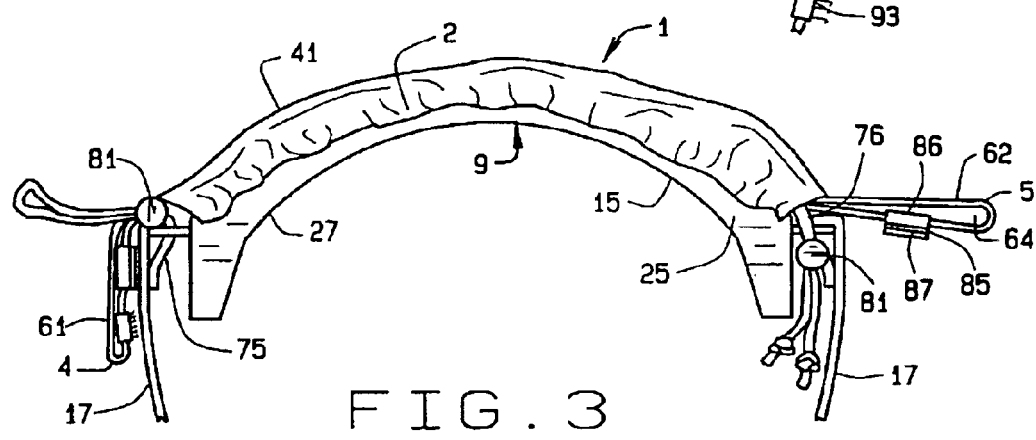
FIG. 3 is a view similar to FIG. 2 showing a second mode of shield attachment to the goggle.

An alternate method of attaching the shield 1 to the goggle 9 with attachment members would be by having the goggle strap 17 extend through the loops 75, 76 of the elastic members 71, 72 (see FIG. 2). The devices 85 are not used in this mode of use. Attachment of the shield 1 to the goggle 9 can also be by a combination of the use of one or more of the loops 75, 76 and one or more of the attachment devices 85 (see FIG. 3). Other modes of attachment may be used through the use of various combinations of loops 75, 76 devices 85 and a fastener described below to form attachment members.

In operation, the shield 1 may be moved to an out of the way position exposing the lens 10 for viewing through by preferably moving the cover 41 upwardly above the goggle 9. The elasticity of the members 71, 72 or the straps 61, 62 will retain the cover 41 in place above the goggle 9. This is particularly effective when the goggle 9 is mounted on a helmet.

Another mode of using the shield 1 is by having one end of the cover 41 attached at one end with an attachment device 85 and/or having the strap 17 be captured within a loop 75 or 76 and having the other end attached only with an attachment device 85. The attachment device 85 is detached from the strap 17 freeing one end of the cover 41 allowing the user to move the free end of the cover 41 in the direction of arrow A to the side and toward the rear of the goggle strap. A fastener device is provided to retain the cover in an out of the way side position. A particularly preferred attachment device is a hook and loop type fastener. Preferably, the hook and loop fastener is in strap form. One portion 92 of the fastener is attached to the strap 61 or 62 that is to be freed. Another portion 93 is preferably attached to the strap 17. Preferably both portions 92 and 93 are similarly constructed and are straps each with a hook face and a loop face. Thus, each of the portions 92, 93 may be attached to itself by having a hook face engage a loop face. As shown, the fastener portion 92 is removably mounted on the strap 61 forming a loop therearound. Preferably, the hook face is exposed and the loop face is inside allowing it to be moved along the strap 61. The fastener portion 93 is removably mounted on the goggle strap 17 and has its loop face exposed and its hook face engaging the strap 17. The hooks on the hook face help retain the fastener portion 93 in a preselected position on the strap 17. The portion 92 is removably attached to the portion 93 to retain the cover 41 to the side and out of the way.

While one embodiment of shield is shown, variations may be provided while still providing the described functional and structural features. For example, the clips 85 are shown in FIG. 1 as having upwardly opening slots 89. By simply inverting the shield 1, the slots would be downwardly opening permitting user preference of mounting and use. Also, one clip may open upwardly and one clip downwardly. The fastener portions 92, 93 may be reversed changing which of the hook or loop face is exposed to also provide for user preference. Reversal is easily accomplished because of their removable attachment. They may also be mounted on either side of the goggle strap 17 and shield 1 to permit moving the cover to a left side or right side of the user.

Figure 6:
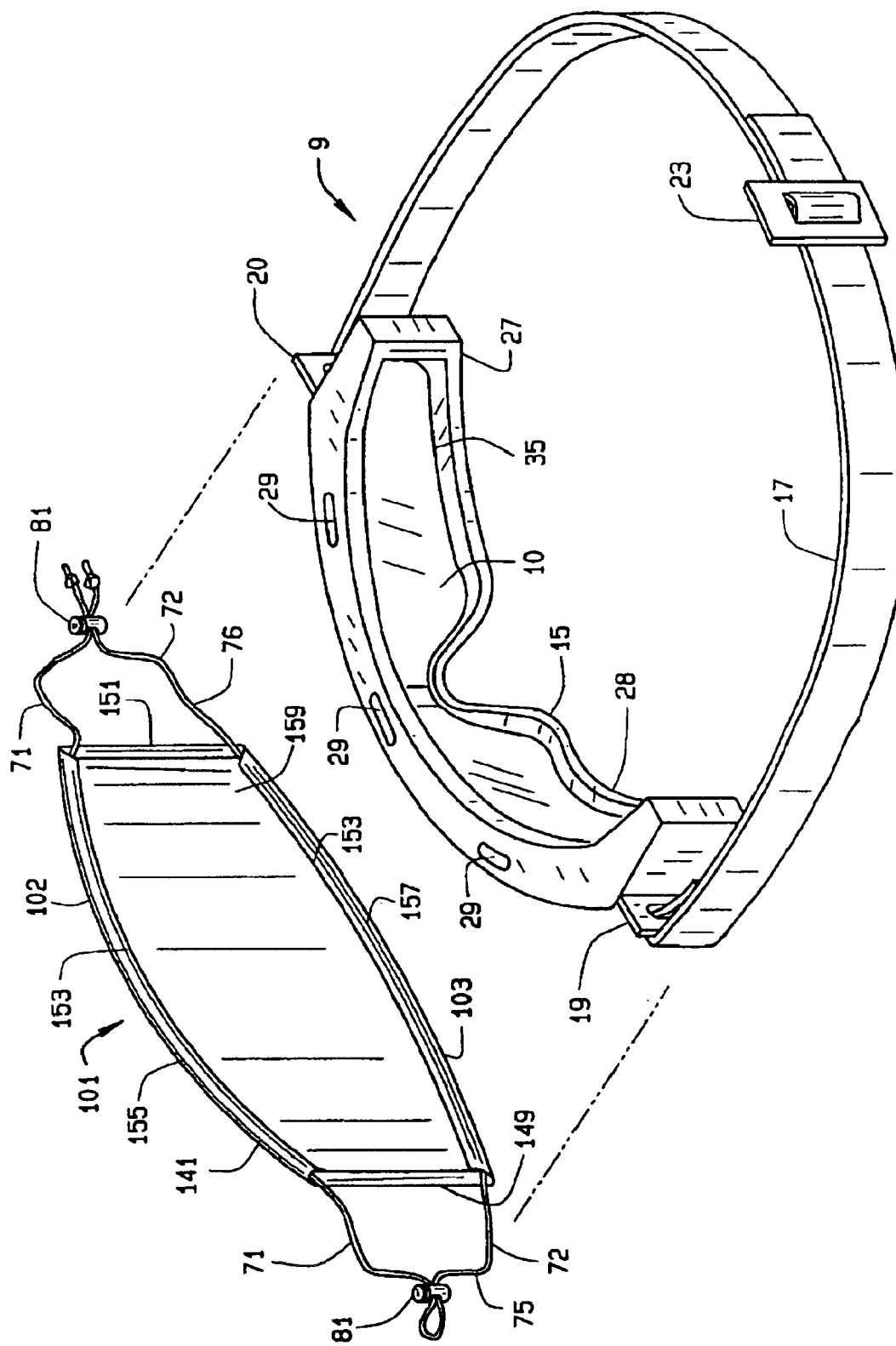
FIG. 6 is a perspective view of an alternative embodiment of a goggle shield and goggle.

FIG. 6 illustrates an alternative embodiment of the present invention which is a simplified version of the shield 1 as shown in FIG. 1. The alternative shield is designated generally as 101. It utilizes the loops 75, 76 for attaching the shield 101 to the goggle 9 as described above. The shield 101 includes top and bottom margins 102, 103 similar to the top and bottom margins 2 and 3 described above. It also includes the upper and lower members 71 and 72 and locks 81. The shield 101 includes a cover 141 similar to the cover 41 described above. The top and bottom margins 102, 103 extend between opposite ends 149, 151. The cover 141 also includes seams 153 similar to the seams 53 described above. Upper and lower channels 155, 157, respectively, are formed at the marginal portions 102, 103 and are similar to the upper and lower channels 55, 57 described above. The cover 141 includes an inside surface 159 and may or may not include a liner 58 as described above and is shown without the liner 58.

One advantageous feature of the present invention is that the shield 1 may be easily installed on a goggle 9 and easily detached from the goggle and carried in a pack or a pocket because of its flexible nature. The shield 1 may also be retained in one of multiple positions on a helmet or a user's head. The shield 1 is relatively inexpensive to manufacture, it is durable and effective in use. It is simple to use, store and transport.

The present invention provides a shield that may be used with existing goggles or may be retrofit on old goggles and it is adjustable to fit many types and sizes of goggles providing universal adaptability.

Thus, there has been shown and described several embodiments of a novel goggle shield. As is evident from the foregoing description, certain aspects of the present invention are not limited by the particular details of the examples illustrated herein and it is therefore contemplated that other modifications and applications, or equivalents thereof, will occur to those skilled in the art. Many changes, modifications, variations and other uses and applications of the present constructions will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed:

1. A goggle shield including:

a cover of flexible material having a top margin, a bottom margin and opposite ends, said top and bottom margins each having an extended length;

an elastic member attached to the cover adjacent to at least one of the top and bottom margins operable to selectively and resiliently shorten said extended length in an adjustable manner;

at least two first attachment members affixed to the cover and operable for removably attaching the cover to a goggle, at least one attachment member being positioned adjacent to a respective cover end said first attachment members being adapted to permit movement of the cover from a position overlying a goggle lens to a position exposing the goggle lens; and wherein said cover is sized and shaped to cover a goggle lens and at least a portion of a goggle body adjacent the lens, said elastic member holding a portion of the cover in sealing engagement with a portion of the goggle said cover being generally in a cup shape when at least one of the extended lengths is resiliently shortened.

2. A shield as set forth in claim 1 including an end strap secured to and extending from each of said opposite ends of the cover and a clip attached to each said strap operable to be removably attached to a respective goggle strap portion.

3. A shield as set forth in claim 2 wherein at least one of said end straps is elastic.

4. A shield as set forth in claim 3 wherein both of said end straps are elastic.

5. A shield as set forth in claim 4 wherein said clips each includes a slide body permanently attached to a respective end strap for movement along the respective end strap and each clip includes a resiliently biased finger forming an open end slot between the body and finger for receipt of a goggle strap portion therein.

6. A shield as set forth in claim 2 including a second attachment member attached to a said end strap and adapted for attachment to a third attachment member attached to a goggle strap to secure the cover in a position exposing a goggle lens extending from an end of a goggle body in overlying relation to a goggle strap.

7. A shield as set forth in claim 6 wherein the second and third attachment members include hook and loop fasteners.

8. A shield as set forth in claim 1 including a first and second said elastic member each attached to the cover adjacent a respective said top or bottom margin and operable to selectively and resiliently shorten the extended length of the respective margin in an adjustable manner.

9. A shield as set forth in claim 8 wherein the top and bottom margins each have a channel extending between the opposite ends of the cover, each elastic member extending through a respective said channel.

10. A shield as set forth in claim 9 wherein said elastic members forming a loop adjacent each end of the cover and adapted to receive a goggle strap portion therethrough for attaching the cover to a goggle allowing the cover to be moved from a position overlying a goggle lens to a position above a goggle body exposing an exterior surface of the goggle lens.

11. A shield as set forth in claim 10 including a lock associated with each said elastic member and operable to adjustably retain the margins at a preselected shortened length.

12. A shield as set forth in claim 11 including a said lock associated with said elastic members adjacent each of said cover ends.

13. A shield as set forth in claim 12 wherein said locks are resiliently biased to a normally locked position.

14. A shield as set forth in claim 1 including a fabric liner secured to said cover for positioning between a goggle lens and the cover.

15. A shield as set forth in claim 14 wherein said liner includes fleece fabric.

16. A shield as set forth in claim 14 wherein said liner includes a microfiber fabric.

17. A removable goggle shield including:
- a cover of flexible fabric having a top margin, a bottom margin and opposite ends said top and bottom margins each having an extended length, a seam at each said margin forming a top and bottom channel;
- at least one elastic member extending through each said channel and forming a loop adjacent each end of the cover;
- a lock cooperating with the at least one elastic member selectively movable therealong to selectively reduce said extended length;
- a strap secured to each end of the cover and extending therefrom;
- a clip attached to each said strap and movable therealong, each clip having a body and a resiliently biased finger forming an open end slot between the finger and body for receipt of a goggle strap portion therein; and
- a first fastener portion attached to a said cover strap and operable for releasable attachment to a second fastener portion attached to a goggle strap.

18. A shield as set forth in claim 17 wherein there is a lock attached to the at least one elastic member at each said loop.

19. A shield as set forth in claim 17 including a fabric liner secured to the cover for positioning between the cover and a goggle lens.

20. A shield as set forth in claim 19 wherein the first fastener portion is a hook or loop type fastener removably attached to a said strap.

21. A goggle shield including:
- a cover of flexible material having a top margin, a bottom margin and opposite ends, said top and bottom margins each having an extended length;
- an elastic member attached to the cover adjacent to at least one of the top and bottom margins operable to selectively and resiliently shorten said extended length in an adjustable manner;
- at least two first attachment members affixed to the cover and operable for removably attaching the cover to a goggle, said first attachment members each including an end strap secured to and extending from each of said opposite ends of the cover and a clip attached to each said strap operable to be removably attached to a respective goggle strap portion; and wherein
- said cover is sized and shaped to cover a goggle lens and at least a portion of a goggle body adjacent the lens, said elastic member holding a portion of the cover in sealing engagement with a portion of the goggle.

22. A shield as set forth in claim 21 wherein at least one of said end straps is elastic.

23. A shield as set forth in claim 22 wherein both of said end straps are elastic.

24. A shield as set forth in claim 23 wherein said clips each includes a slide body permanently attached to a respective end strap for movement along the respective end strap and each clip includes a resiliently biased finger forming an open end slot between the body and finger for receipt of a goggle strap portion therein.

25. A shield as set forth in claim 21 including a second attachment member attached to a said end strap and adapted for attachment to a third attachment member attached to a goggle strap to secure the cover in a position exposing a goggle lens extending from an end of a goggle body in overlying relation to a goggle strap.

26. A shield as set forth in claim 25 wherein the second and third attachment members include hook and loop fasteners.

* * * * *